United States Patent
Kenning et al.

(10) Patent No.: US 7,443,951 B2
(45) Date of Patent: Oct. 28, 2008

(54) EXEMPT SOURCE FOR AN X-RAY FLUORESCENCE DEVICE

(75) Inventors: Donald K. Kenning, Kennewick, WA (US); L. Stephen Price, Richland, WA (US); Bruce J. Kaiser, Richland, WA (US)

(73) Assignee: KeyMasters Technologies, Inc., Kennewick, WA (US)

( * ) Notice: Subject to any disclaimer, the term of this patent is extended or adjusted under 35 U.S.C. 154(b) by 0 days.

(21) Appl. No.: 11/097,018

(22) Filed: Apr. 1, 2005

(65) Prior Publication Data

US 2006/0039530 A1    Feb. 23, 2006

Related U.S. Application Data

(63) Continuation-in-part of application No. PCT/US2004/009747, filed on Mar. 31, 2004.

(60) Provisional application No. 60/459,747, filed on Apr. 1, 2003.

(51) Int. Cl.
G01N 23/223 (2006.01)
H01J 35/16 (2006.01)
H05G 1/10 (2006.01)
(52) U.S. Cl. .................. 378/44; 378/203; 378/102
(58) Field of Classification Search ............ 378/42–54, 378/102, 119, 57, 203
See application file for complete search history.

(56) References Cited

U.S. PATENT DOCUMENTS 2,957,079 A    10/1960    Edholm
3,992,794 A    11/1976    Lazarus
4,054,676 A    10/1977    Weinshenker et al.
4,136,778 A     1/1979    Wortman et al.
4,251,726 A     2/1981    Alvarez
4,363,965 A    12/1982    Soberman et al.
4,390,452 A     6/1983    Stevens
4,445,225 A     4/1984    White
4,476,382 A    10/1984    White
4,485,308 A    11/1984    Rabatin
4,767,205 A     8/1988    Schwartz et al.
4,862,143 A     8/1989    Hirshfield et al.

(Continued)

FOREIGN PATENT DOCUMENTS

EP    0911626 A1    4/1999

(Continued)

OTHER PUBLICATIONS

U.S. Appl. No. 11/097,018, filed Apr. 1, 2005, Kenning et al.

(Continued)

Primary Examiner—Irakli Kiknadze

(57) ABSTRACT

An x-ray fluorescence (XRF) device and a method for using the same to analyze a sample are described. The EMRXG source of the XRF device has a configuration that allows a greater amount of EMRXG to impinge on the sample being analyzed. The x-ray detector of the XRF device has a configuration that allows a greater amount of x-rays emitted by the sample to impinge on the detector. With such a configuration, the size and cost of the x-ray fluorescence device decreases. As well, fewer EMRXG are needed from the EMRXG source because of the greater efficiency and an exempt EMRXG source that is exempt from radioactivity licensing requirements can be used.

25 Claims, 9 Drawing Sheets

U.S. PATENT DOCUMENTS

| | | | |
|---|---|---|---|
| 5,057,268 A | 10/1991 | Muller | |
| 5,185,773 A | 2/1993 | Blossfeld et al. | |
| 5,202,931 A * | 4/1993 | Bacus | 382/133 |
| 5,208,630 A | 5/1993 | Goodbrand et al. | |
| 5,301,044 A | 4/1994 | Wright | |
| 5,461,654 A | 10/1995 | Grodzins et al. | |
| 5,474,937 A | 12/1995 | Anderson, II et al. | |
| 5,527,707 A | 6/1996 | Fukazawa | |
| 5,670,239 A | 9/1997 | Hampp | |
| 5,677,187 A | 10/1997 | Anderson, II et al. | |
| 5,692,029 A | 11/1997 | Husseiny et al. | |
| 5,740,223 A | 4/1998 | Ozawa et al. | |
| 5,760,394 A | 6/1998 | Welle | |
| 5,830,769 A | 11/1998 | Wieder et al. | |
| 5,849,590 A | 12/1998 | Anderson, II et al. | |
| 6,005,915 A | 12/1999 | Hossain et al. | |
| 6,007,744 A | 12/1999 | Nacker | |
| 6,024,200 A | 2/2000 | Jang | |
| 6,030,657 A | 2/2000 | Butland et al. | |
| 6,041,095 A | 3/2000 | Yokhin | |
| 6,075,839 A | 6/2000 | Treseder | |
| 6,082,775 A | 7/2000 | Phillips | |
| 6,097,785 A | 8/2000 | Elam | |
| 6,106,021 A | 8/2000 | Phillips | |
| 6,111,929 A * | 8/2000 | Hazlett | 378/45 |
| 6,130,931 A | 10/2000 | Laurila et al. | |
| 6,165,609 A | 12/2000 | Curatolo | |
| 6,178,226 B1 | 1/2001 | Hell et al. | |
| 6,178,227 B1 | 1/2001 | Sato | |
| 6,200,239 B1 | 3/2001 | Kennedy, III et al. | |
| 6,200,628 B1 | 3/2001 | Rozumek et al. | |
| D460,370 S | 7/2002 | Kaiser et al. | |
| 6,477,227 B1 | 11/2002 | Kaiser et al. | |
| 6,501,825 B2 | 12/2002 | Kaiser et al. | |
| 6,631,177 B1 * | 10/2003 | Haszler et al. | 378/50 |
| 6,668,039 B2 * | 12/2003 | Shepard et al. | 378/47 |
| 6,670,239 B2 | 12/2003 | Yoon | |
| 6,765,986 B2 * | 7/2004 | Grodzins et al. | 378/46 |
| 6,850,592 B2 | 2/2005 | Schramm et al. | |
| 6,859,517 B2 * | 2/2005 | Wilson et al. | 378/47 |
| 6,909,770 B2 | 6/2005 | Schramm et al. | |
| 2002/0168045 A1 * | 11/2002 | Grodzins et al. | 378/45 |
| 2003/0048877 A1 * | 3/2003 | Price et al. | 378/203 |

FOREIGN PATENT DOCUMENTS

| | | |
|---|---|---|
| EP | 0911627 A1 | 4/1999 |
| WO | WO02/068945 A1 | 9/2002 |

OTHER PUBLICATIONS

Keegan, "Applying Data Matrix Identification Symbols on Aerospace Parts," NASA Technical Standard NASA-STD-6002, Jul. 2, 2001.

Keegan, "Application of Data Matrix Identification Symbols on Aerospace Parts Using Direct Part Marking Methods/Techniques," NASA-Technical Handbook NASA-HDBK-6003, Jul. 2, 2001.

* cited by examiner

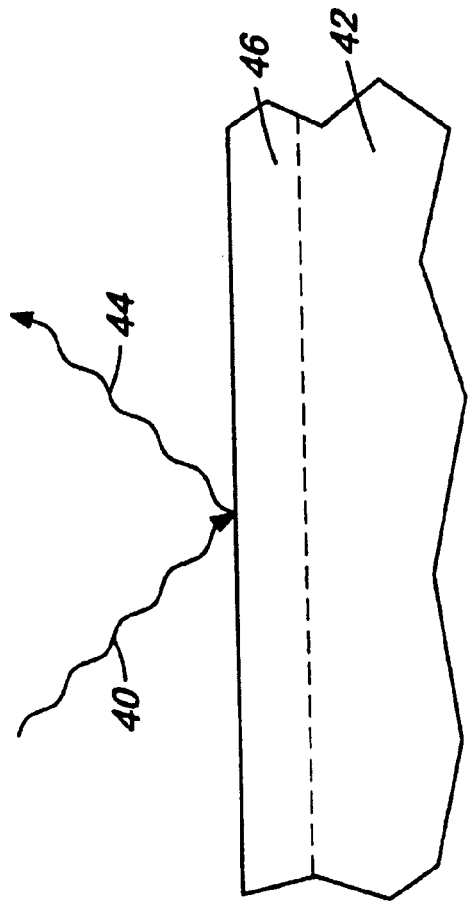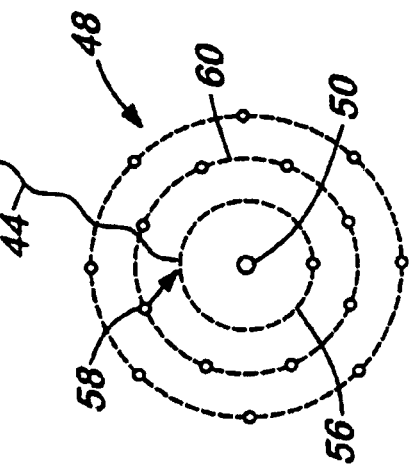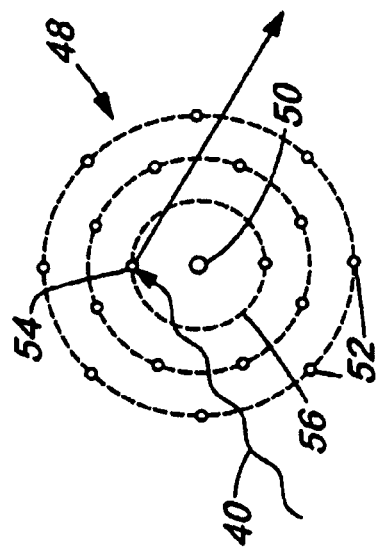

EXEMPT SOURCE FOR AN X-RAY FLUORESCENCE DEVICE

CROSS REFERENCE TO RELATED APPLICATIONS

This application is a continuation-in-part of International Application No. PCT/US2004/009747 filed Mar. 31, 2004 which claims priority to U.S. Provisional Patent Application No. 60/459,747 filed Apr. 1, 2003.

BACKGROUND OF THE INVENTION

This invention relates generally to devices using electromagnetic radiation x-rays and/or gamma rays (EMRXG) and methods for using the same. More particularly, this invention relates to an exempt EMRXG source that can be used in an x-ray fluorescence device, including a portable x-ray fluorescence device, and a method for using the same.

There has been significant interest in apparatus and methods for identifying and verifying various materials or products such as explosives, ammunition, paint, petroleum products, and documents. Known methods used to identify and verify generally involve adding and detecting materials like code-bearing microparticles, bulk chemical substances, and radioactive substances or using the material element constituents. Other methods used for identifying and verifying materials include those described in U.S. Pat. Nos. 6,501,825, 6,477,227, 6,200,239, 6,030,657, 6,024,200, 6,007,744, 6,005,915, 5,849,590, 5,760,394, 5,677,187, 6,670,239, 5,474,937, 5,301,044, 5,208,630, 5,057,268, 4,862,143, 4,390,452, 4,363,965, and 4,045,676, as well as European Patent Application Nos. 0911626, 0911627, and 02723211.5.

It is also known to apply materials to articles in order to track, for example, point of origin, authenticity, and their distribution. In one method, inks that are transparent in visible light are sometimes applied to materials and the presence (or absence) of the ink is revealed by ultraviolet or infrared fluorescence. Other methods include implanting microscopic additives that can be detected optically. However, detecting these materials is primarily based on optical or photometric measurements.

Numerous devices are known for identifying and verifying articles containing such materials (called taggants) by x-ray fluorescence (XRF). See, for example, U.S. Pat. Nos. 5,461,654, 6,130,931, 6,041,095, 6,075,839, 6,097,785, and 6,111,929. Unfortunately, many of the known apparatus are unsatisfactory for several reasons. First, they are often difficult and time-consuming to use. In many instances, a sample of the article must be sent to an off-site laboratory for analysis. In other instances, the apparatus are often expensive, large, and difficult to operate. For example, the known apparatus and methods for identification and verification are also unsatisfactory because the devices employed are usually not portable.

Second, the known devices are unsatisfactory because of the governmental licensing requirements needed for the EMRXG sources used in XRF devices. The EMRXG sources are radioactive and are regulated by numerous governmental entities because of the amount of radioactivity. While x-ray tubes, which are not radioactive, can be used as an x-ray source in XRF devices, they are often not used because XRF devices containing them are still quite large and are very expensive.

SUMMARY OF THE INVENTION

The invention provides an x-ray fluorescence (XRF) device and a method for using the same to analyze a sample. The EMRXG source of the XRF device has a configuration that allows a greater amount of x-rays and/or gamma rays to impinge on the sample being analyzed. The x-ray detector of the XRF device has a configuration that allows a greater amount of x-rays emitted by the sample to impinge on the detector. With such a configuration, the size and cost of the x-ray fluorescence device decreases. As well, fewer EMRXG are needed from the EMRXG source because of the greater efficiency and an exempt EMRXG source (exempt from radioactivity licensing requirements) can be used.

BRIEF DESCRIPTION OF THE DRAWINGS

FIGS. 1, 2a, 2b, 3, 4a, 4b, and 5-12 are views of one aspect of the XRF devices and methods of using such devices according to the invention, in which:

FIG. 1 generally depicts the operation of XRF;

FIGS. 2a and 2b illustrate the operation of XRF at the molecular level;

FIG. 3 shows an exemplary x-ray spectrum, e.g., for paper;

FIGS. 4a and 4b depict two aspects of the XRF apparatus of the invention;

FIG. 5 illustrates exemplary energy levels of x-rays in an x-ray spectrum;

FIG. 6 shows another aspect of the XRF apparatus of the invention;

FIG. 7 illustrates yet another aspect of the XRF apparatus of the invention;

FIGS. 8-11 illustrate various configurations for the EMRXG source of the invention; and FIG. 12 illustrates still another aspect of the XRF apparatus of the invention.

FIGS. 1, 2a, 2b, 3, 4a, 4b, and 5-12 illustrate specific aspects of the invention and are a part of the specification. Together with the following description, the Figures demonstrate and explain the principles of the invention and are views of only particular, rather than complete, portions of the invention.

DETAILED DESCRIPTION OF THE INVENTION

Figure 3:
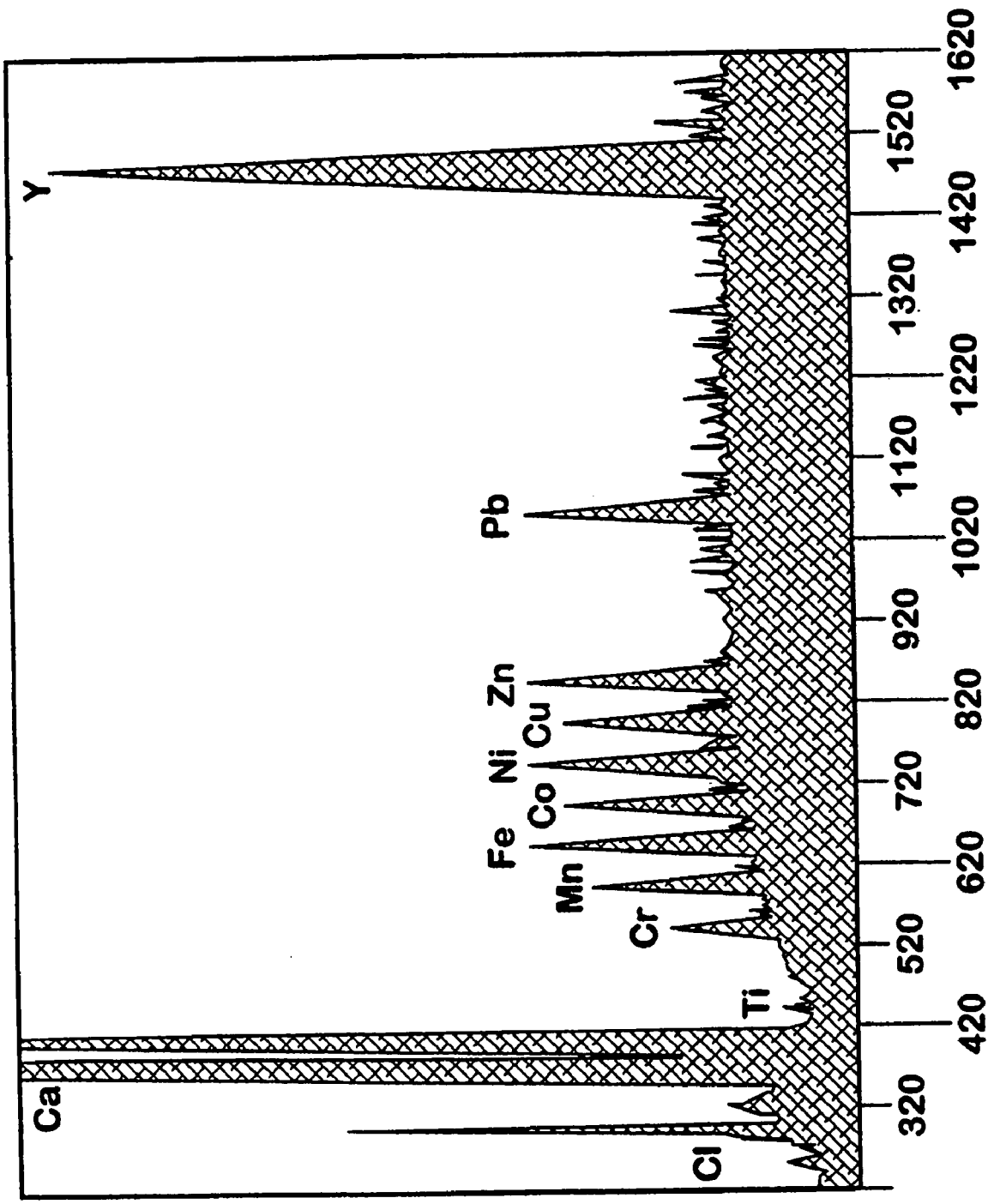

The following description provides specific details in order to provide a thorough understanding of the invention. The skilled artisan would understand, however, that the invention can be practiced without employing these specific details. Indeed, the invention can be practiced by modifying the illustrated apparatus and method and can be used in conjunction with apparatus and techniques conventionally used in the industry. For example, the invention is described with respect to using the EMRXG source (and method) in a portable XRF device. The invention described below, however, could be easily modified for devices other than XRF devices, such as benchtop XRF systems and EMRXG devices.

In one aspect, the invention uses x-ray fluorescence analysis to detect and analyze the element(s) of a product or article. With x-ray fluorescence (XRF) analysis, high energy radiation (e.g., x-rays) produced from electron shifts in the inner shell(s) of atoms of the elements and, therefore, are not affected by the form (chemical bonding) of the article being analyzed. The x-rays emitted from each element bear a specific and unique spectral signature, allowing one to determine whether that specific element is present in the product or article. In one aspect of the invention, the element is a taggant that is used to "tag" the product or article. In other aspects of the invention, the elemental composition of the sample is being determined.

FIGS. 1, 2a, and 2b represent how it is believed XRF generally operates. In FIG. 1, primary gamma rays and/or or x-rays (EMRXG) 40 are irradiated on a sample of a target material 46 of article 42. Secondary gamma rays and/or x-rays 44 are emitted or back-scattered from the sample of target material 46. Since XRF primarily deals with x-ray irradiation and detection, the following description will refer to x-rays. But the invention also encompasses irradiation and detection of gamma rays.

In FIGS. 2a and 2b, atom 48 within target material 46 has nucleus 50 surrounded by electrons 52 at discrete distances from nucleus 50 (called electron shells). Each electron shell has a binding energy level equal to the amount of energy required to remove that electron from its corresponding shell. The innermost shell is the K shell, and has the highest binding energy level associated with it. Electron 54 is located within K shell 56.

Primary x-ray or gamma ray photon 40 impacting atom 48 has a given energy. If that energy is greater than the binding energy level of K shell 56, the energy of x-ray photon 40 is absorbed by atom 48, and one of the electrons in K shell 56 (i.e., electron 54) is ejected from atom 48. With a vacancy now in K shell 56 left by electron 54, atom 48 is energetic and unstable. To become more stable, that vacancy in K shell 56 can be, and usually is, filled by an electron located in a shell with a higher binding energy level, such as L-shell electron 58 in L shell 60. As L-shell electron 58 fills the vacancy in K shell 56, atom 48 emits a secondary x-ray photon 44. The energy levels, or corresponding wavelengths, of such secondary x-ray photons are uniquely characteristic to each atom, allowing the presence or absence of any specific element to be determined.

As shown in FIG. 3, the x-rays which are detected have various energies, e.g., there is a broad band of scattered EMRXG with energies less than and greater than those of the excited atom(s). FIG. 3 illustrates this spectrum for paper as the target material. Within this broad band, there are peaks due to the excitation of the element(s) in the sample. The ratio of the intensity of the radiation in any peak to the intensity of the background at the same energy (known as the peak-to-background ratio) can be used as a measure of the concentration of the element which has characteristic X-rays at the energy of that peak, for example, the taggant.

In one aspect of the detection method of the invention, at least one target material believing to contain known concentrations of the element(s) of interest is selected. The XRF analysis is performed on that target material (or a sample thereof) using a detection device or apparatus containing an EMRXG source ("source"), x-ray detector ("detector"), support means, analyzer means, and calibration means.

Figure 4A:
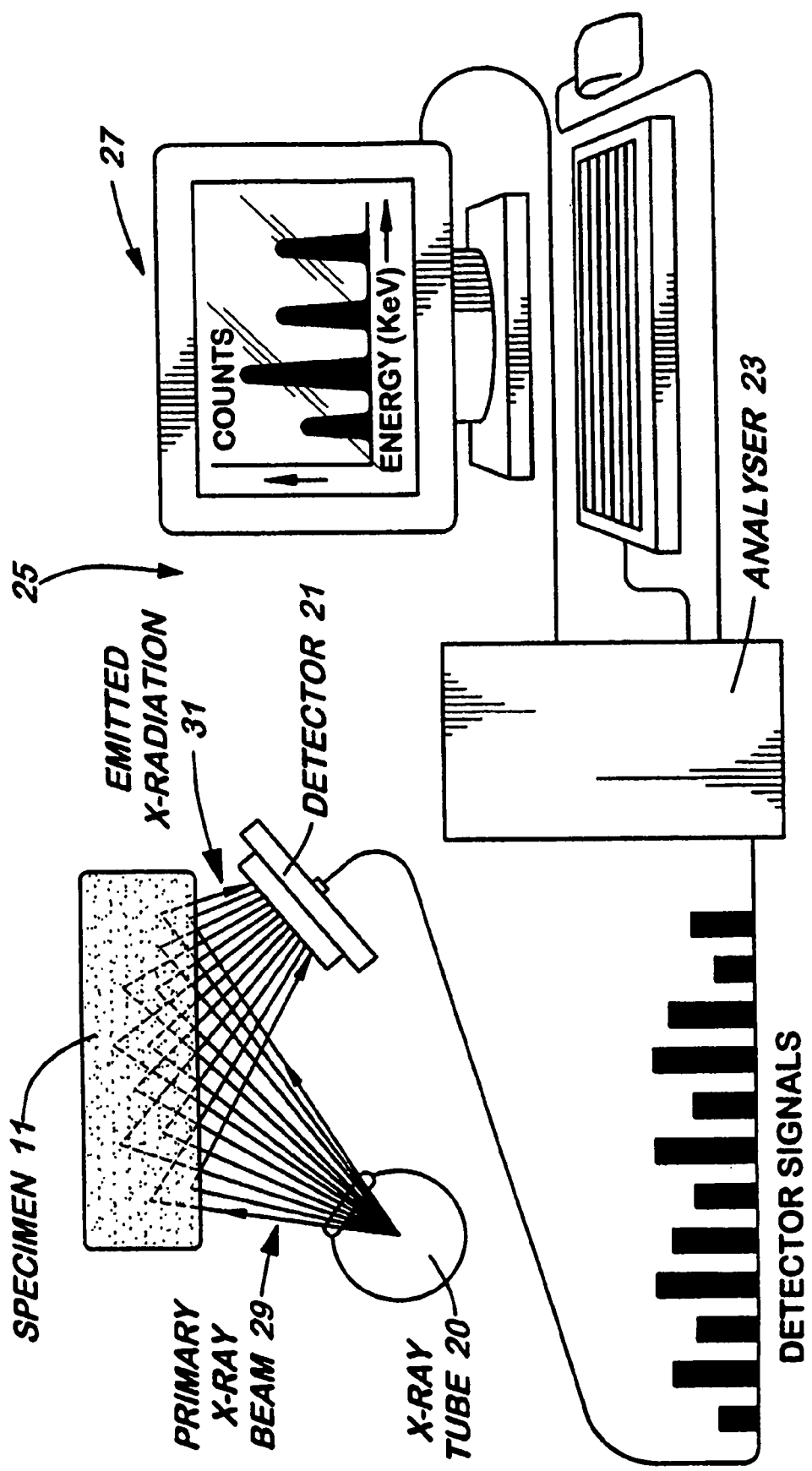

One aspect of the detection device of the invention is illustrated in FIG. 4a. In this Figure, the detection apparatus 25 has an ordinary x-ray fluorescence spectrometer capable of detecting elements present in a coating, package or material. X-ray's 29 from a source 20, for example, either x-ray tube or radioactive isotope, impinge on a sample 11 which absorbs the radiation and emits x-rays 31 to an x-ray detector 21 and analyzer 23 capable of energy or wavelength discrimination. This is accomplished by using a commercially available x-ray spectrometer such as an Edax DX-95 or a MAP-4 portable analyzer, commercially available from KeyMaster Technologies, Inc. Kennewick, Wash. Part of analyzer 23 includes a computerized system 27.

Figure 4B:
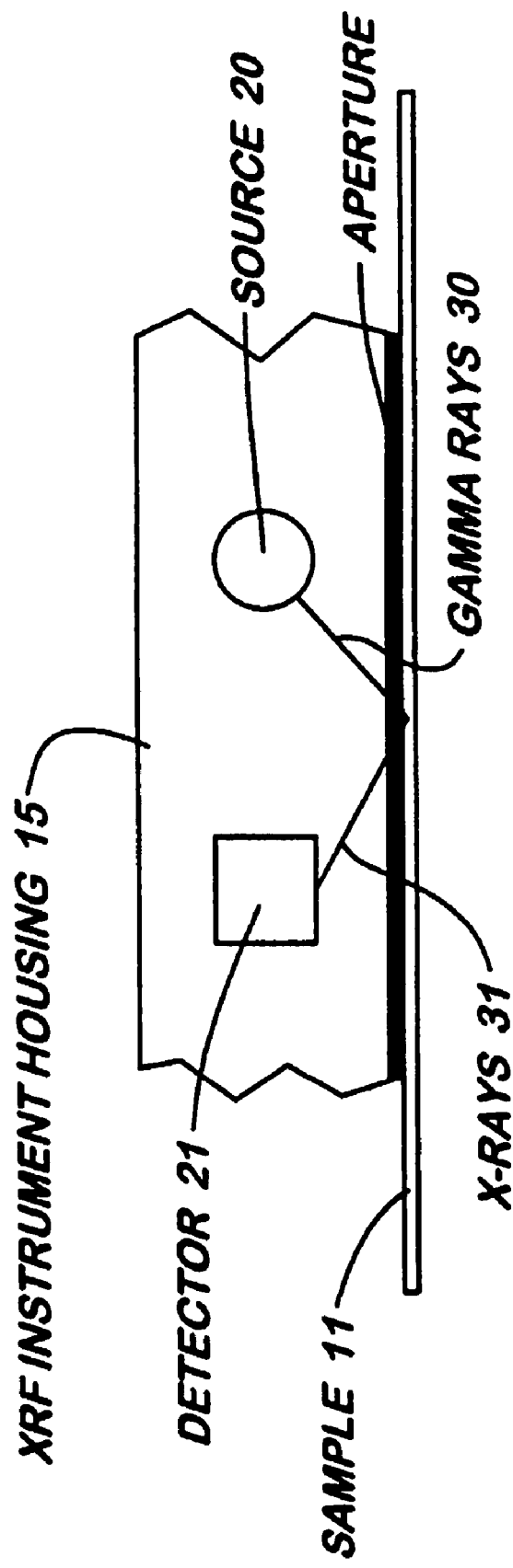

Another aspect of the detection apparatus of the invention is illustrated in FIG. 4b. In this Figure, the detection apparatus 25 has an external housing 15 which contains the various components. Gamma rays or x-rays 30 from a source 20, for example, either x-ray tube or radioactive isotope, are optionally directed by aperture 10 to impinge on a sample 11. Sample 11 contains the at least one element, or taggant, which absorbs the radiation and emits x-rays 31 to an x-ray detector 21. Optionally, analyzing means can be incorporated within housing 15.

The invention, however, is not limited to the detection apparatus depicted in FIGS. 4a and 4b. Any suitable source, or plurality of sources, known in the art can be used as the source in the device of the invention. See, for example, U.S. Pat. Nos. 4,862,143, 4,045,676, 6,178,226, and 6,005,915, the disclosures of which are incorporated herein by reference. During the XRF detection process, the source bombards the element(s) with a high energy radiation, often in the form of a beam. The high energy radiation may be an electron beam or electromagnetic radiation such as X-rays or gamma rays. The source, therefore, may be any material emitting such high energy radiation. Typically, these have been EMRXG emitting devices such as x-ray tubes or radioactive sources.

To target, the radiation (e.g., beam) can be focused and directed properly by any suitable means such as an orifice or an aperture. The configuration (size, length, diameter) of the beam is controlled, as known in the art, to obtain the desired XRF detection. The power, or energy level, of the source is controlled, as known in the art, to obtain the desired XRF detection.

The source(s) can be shielded and emit radiation in a space limited by the shape of the shield. In one aspect of the invention, this shield is a source block, as described below. Thus, the presence, configuration, and the material used for shielding the source should be controlled for consistent XRF detection. Any suitable material and configuration for that shield known in the art can be employed in the invention. Preferably, any high-density materials used as the material for the shield, e.g, tungsten or brass.

Any suitable detector, or plurality of detectors, known in the art can be used as the detector in the detection device of the invention. See, for example, U.S. Pat. Nos. 4,862,143, 4,045,676, and 6,005,915. Any type of material capable of detecting the photons omitted by the element(s) can be used. Silicon and CZT (cadmium-zinc-telluride) detectors have been conventionally used, but others such as proportional counters, germanium detectors, or mercuric iodide crystals can be used.

Several aspects of the detector should be controlled to obtain the desired XRF detection. First, as described below, the geometry between the detector and the target (and between the source and the target) should be controlled. The XRF detection also depend on the presence, configuration, and material, for example, beryllium, used as a window to allow x-rays photons to strike the detector. The age of the detector, voltage, humidity, variations in exposure, and temperature can also impact the XRF detection and, therefore, these conditions should be controlled.

The analyzer means sorts the radiation detected by the detector into one or more energy bands and measures its intensity. Thus, any analyzer means performing this function could be used in the invention. The analyzer means can be a multi-channel analyzer for measurements of the detected radiation in the characteristic band and any other bands necessary to compute the value of the characteristic radiation as distinguished from other elements or scattered or background radiation. See, for example, U.S. Pat. Nos. 4,862,143, 4,045,676, and 6,005,915, the disclosures of which are incorporated herein by reference.

The XRF analysis somewhat depends on the ability of the components of the XRF device to resolve the energies of the photons being detected. Background and other noise must be filtered for proper measurement, for example, the signals must be separated into the proper number of channels and excess noise removed. The resolution can be improved by cooling the detector using a thermoelectric cooler, for example, a peltier cooler, and/or by other means. Another way to improve this resolution is to use pre-amplifiers.

The support means supports the source and detector in predetermined positions relatively to a sample of the target material to be irradiated. Thus, any support means performing this function could be used in the invention. In one example, the support means comprises two housings, where the source and detector are mounted in a first housing which is connected by a flexible cable to a second housing in which the analyzer means is positioned as illustrated in FIG. 4a. If desired, the first housing may then be adapted to be hand-held. In another example, the source and detector as well as the other components of the detection device are mounted in a single housing as illustrated in FIG. 4b.

Analyzer means, which includes a computerized system 27, is coupled to, receives, and processes the output signals produced by the detector and/or preamplifier. The energy range of interest, which includes the energy levels of the secondary x-ray photons 44 emitted by the element(s), is divided into several energy subranges. Computerized system 27 maintains counts of the number of X-ray photons detected within each subrange using specific software programs, such as those to analyze the detection and x-ray interaction and to analyze backscatter data. After the desired exposure time, computerized system 27 with display menus stops receiving and processing output signals and produces a graph of the counts associated with each subrange. This graph is often called a spectrum.

Figure 5:
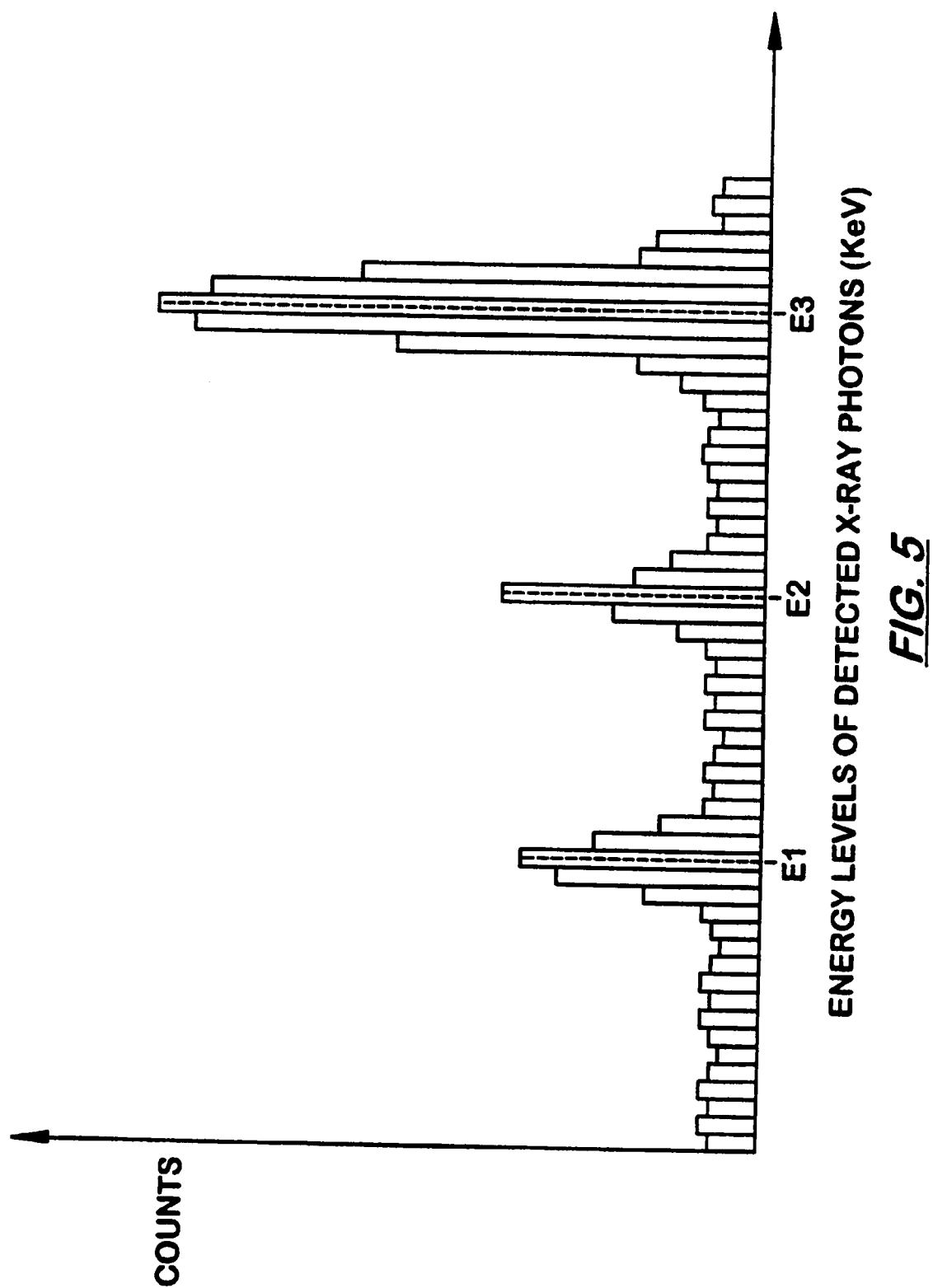

FIG. 5 is a representative graph of the counts associated with each subrange. This graph is essentially a histogram representing the frequency distribution of the energy levels E1, E2, and E3 of the detected high energy radiation, e.g., x-ray photons. Peaks in the frequency distribution (i.e., relatively high numbers of counts) occur at energy levels of scattered primary EMRXG photons as well as the secondary x-ray photons from the taggant(s) or sample being analyzed. A primary EMRXG photon incident upon a target material may be absorbed or scattered. The desired secondary x-ray photons are emitted only when the primary EMRXG photons are absorbed. The scattered primary EMRXG photons reaching the detector of the system create a background intensity level. Accordingly, the sensitivity of XRF analysis is dependent on the background intensity level, and the sensitivity of XRF detection may be improved by reducing the amount of scattered primary EMRXG photons reaching the detector. While the peak occurring at energy levels of scattered primary EMRXG photons is present, the other peaks, those occurring at E1, E2, and E3, are used to identify the at least one taggant present in the target material or to analyze the amount of the element(s) present in a sample.

Besides the parameters described above, at least two other parameters must be controlled during the process of XRF detection. First, the media (such as air) through which the gamma rays (and x-rays) must travel also impacts the XRF analysis. Therefore, the different types of media must be considered when performing the XRF analysis. Second, the methods used to interpret and analyze the x-rays depend, in large part, on the algorithms and software used. Thus, methods must be adopted to employ software and algorithms that will consistently perform the XRF analysis.

Figure 6:
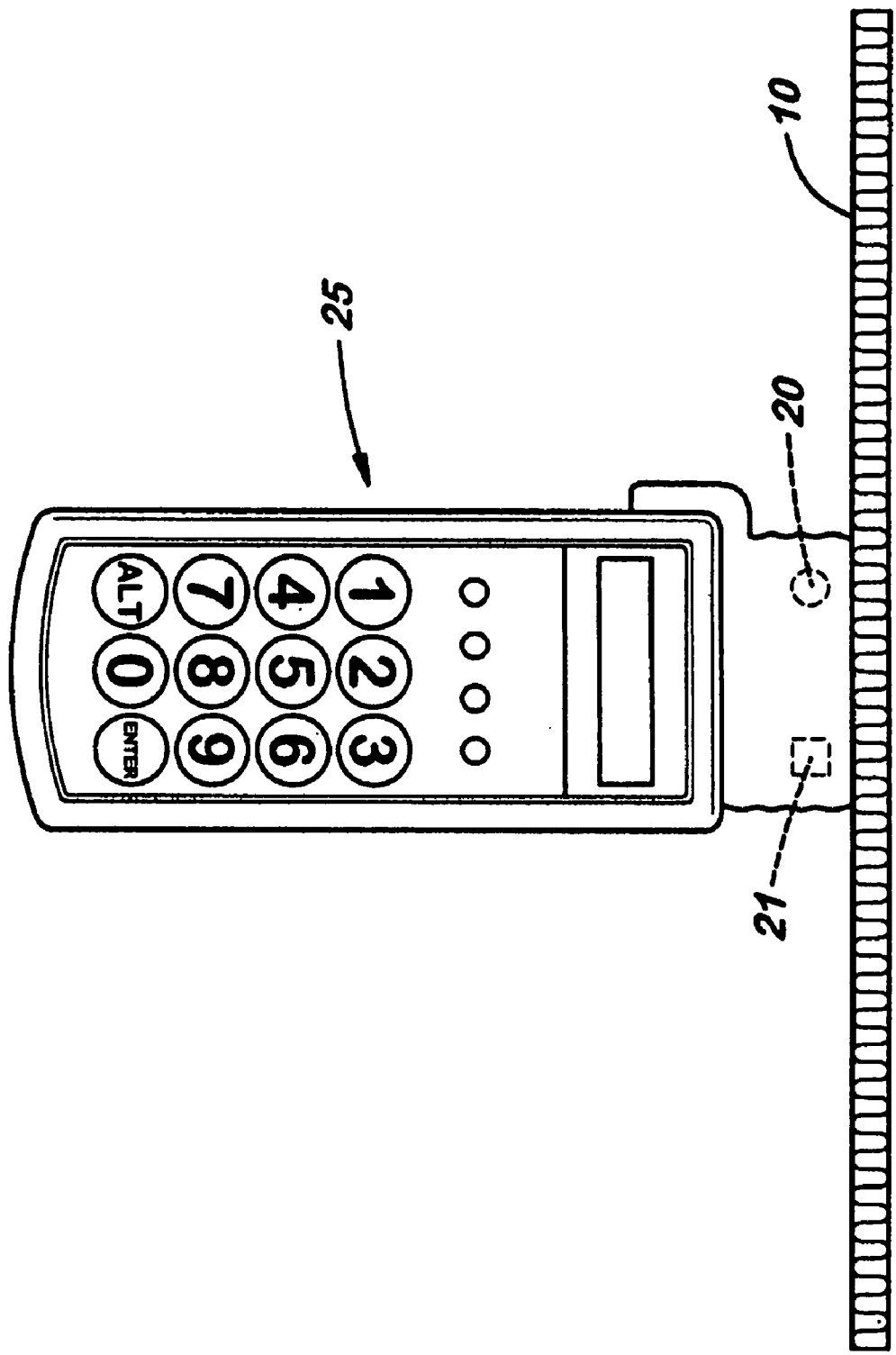

FIG. 6 illustrates an apparatus and detection method according to one aspect of the invention. In FIG. 6, detection apparatus 25 is capable of detecting at least one element or taggant present in target material 10. Detection apparatus 25 is a portable device that is small enough to be hand-held. Detection apparatus 25 contains all the components discussed above, for example, source, detector, analyzer means, and calibration means, in a single external housing, thus allowing the portability and smaller size.

Figure 7:
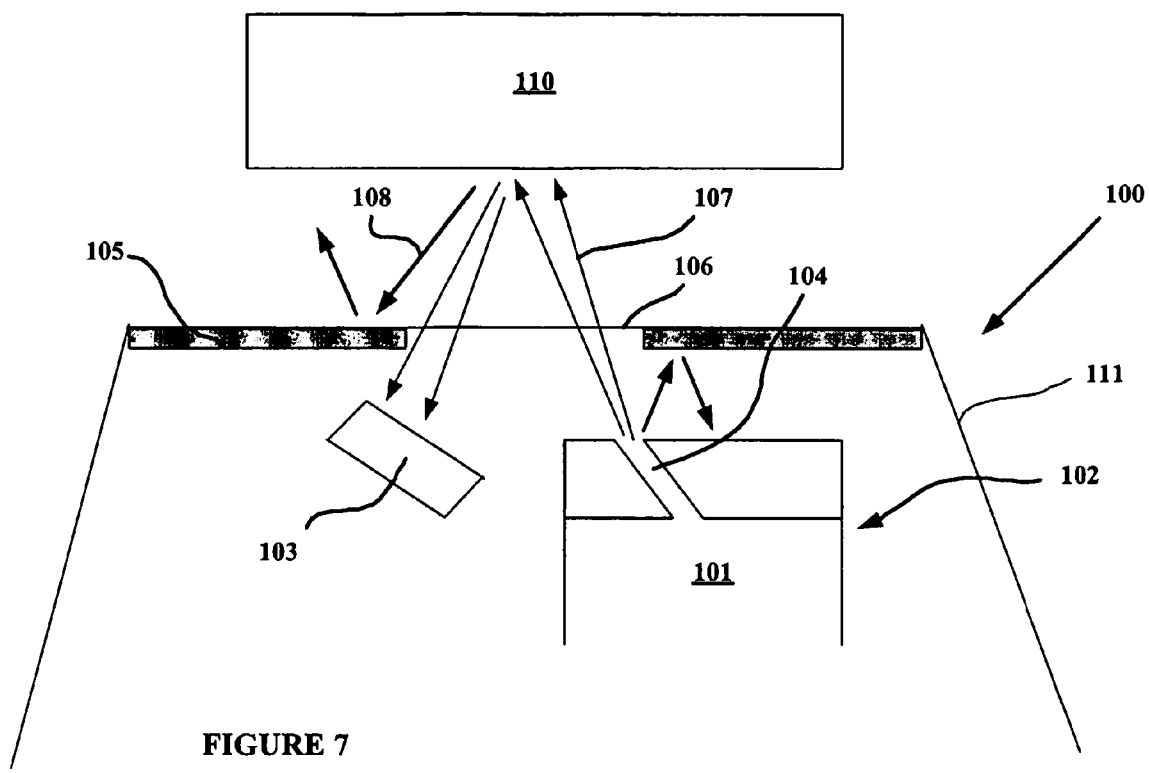
Figure 8:
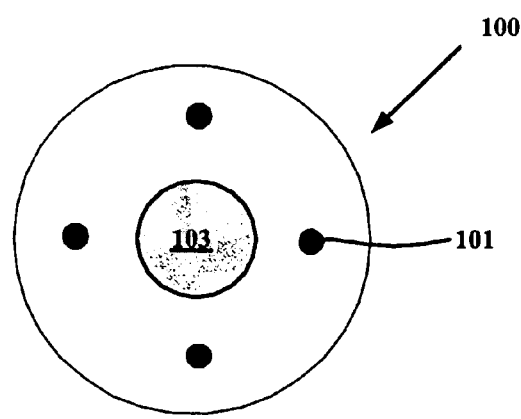
Figure 9:
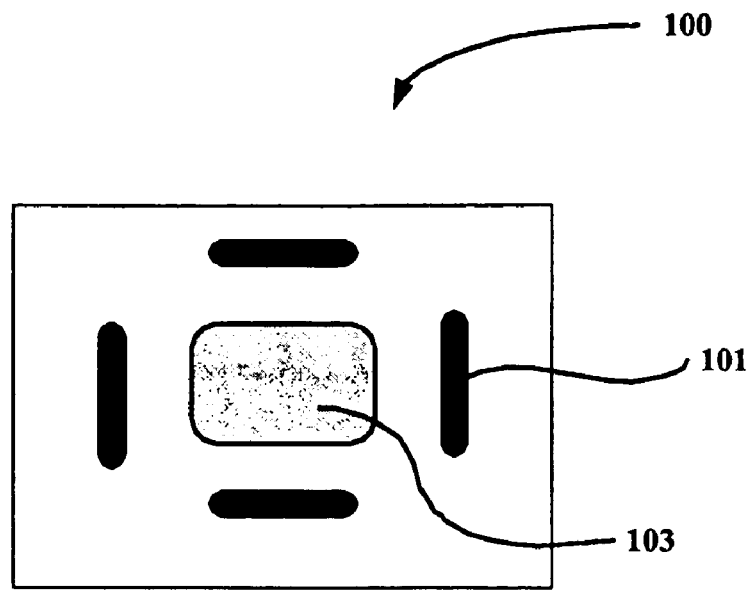

In one aspect of the invention, the EMRXG source is a source that is configured to allow a large amount of EMRXG to impinge on the sample to be analyzed. To increase the amount of EMRXG impinged on the sample, the location of the source is removed from the locations depicted in FIG. 4b and FIG. 6 (a close-up of which is illustrated in FIG. 7). In FIG. 7, XRF device 100 is used to analyze a sample 110. The XRF device 100 contains an external housing 111 encompassing detector 103, as well as EMRXG source 101 located within the source block 102. The source 101 emits EMRXG 107 through the channel or aperture 104 located within the source block 102. Some of the EMRXG 107 pass through the window 106 while the remainder of the EMRXG are prevented from reaching the samples 110 by block 105. Some of the x-rays 108 that fluoresce from the sample impinge on detector 103 while the remainder are prevented from reaching the detector by block 105.

Of the EMRXG that are emitted from the source 101 in this configuration, only a small percentage are able to impinge on the sample. Typically, only about $\frac{1}{300}^{th}$ or less of the EMRXG emitted from the radioactive source 101 impinge on the sample 110. Further, of the x-rays that fluoresce from the sample, only a small percentage impinge on the detector 103.

As well, in such a configuration as depicted in FIG. 7, the XRF device is located a distance (d) away from the sample during operation to analyze the sample. This distance is typically greater than about 0.5 cm because it is difficult to position the detector/source close to the sample with that configuration. Thus, to obtain the desired amount of EMRXG needed to fluoresce the sample 110 with the XRF device illustrated in FIG. 7, the source must be highly radioactive. With such high levels of radioactivity, the EMRXG source becomes regulated by governmental licensing requirements.

In the invention, the EMRXG source is configured to allow a greater amount of EMRXG to impinge on the sample. Typically, about 20% to about 50% of the EMRXG emitted from the source impinge on the sample in the invention. In one aspect of the invention, this amount is about 30%. With more EMRXG striking the sample, more x-rays are fluoresced from the sample and strike the detector. Thus, the increase in EMRXG impinging on the sample indicated above can yield a corresponding increase in the amount of x-rays detected. Thus, the invention is able to achieve an overall increase of about 100 to about 1000 times in the efficiency of the XRF device.

Thus, to obtain the same result as the device in FIG. 7, the EMRXG source in the invention need not emit as many EMRXG because the XRF device is more efficient in terms of EMRXG striking the sample (and therefore the number of fluoresced x-rays from the sample). This increased efficiency is especially helpful where a radioactive source is used. To obtain the desired amount of EMRXG needed to fluoresce the sample, the source quantity is much smaller and, therefore, is less regulated by governmental licensing requirements.

Any configuration of the XRF device that allows this increased efficiency and increased amount of EMRXG striking the sample and being fluoresced can be used in the invention. In one aspect of the invention, this result is obtained by eliminating the source block containing the source. The source is moved to the portion of the XRF device containing the detector. In one aspect of the invention, the source has been moved to a location on the XRF device as close as possible to the sample. Being as close as possible to the sample maximizes the amount of EMRXG emitted from the source that can impinge on the sample.

In another aspect of the invention, the XRF device is configured to allow an increased amount of x-rays emitted from the sample to impinge on the detector. To increase the amount of x-rays impinged on the detector, the location of the detector was removed from the location depicted in FIG. 7. The detector is moved to the portion of the XRF device containing the source as close as possible to the sample. Being as close as possible to the sample maximizes the amount of x-rays that can impinge on the detector.

Figure 12:
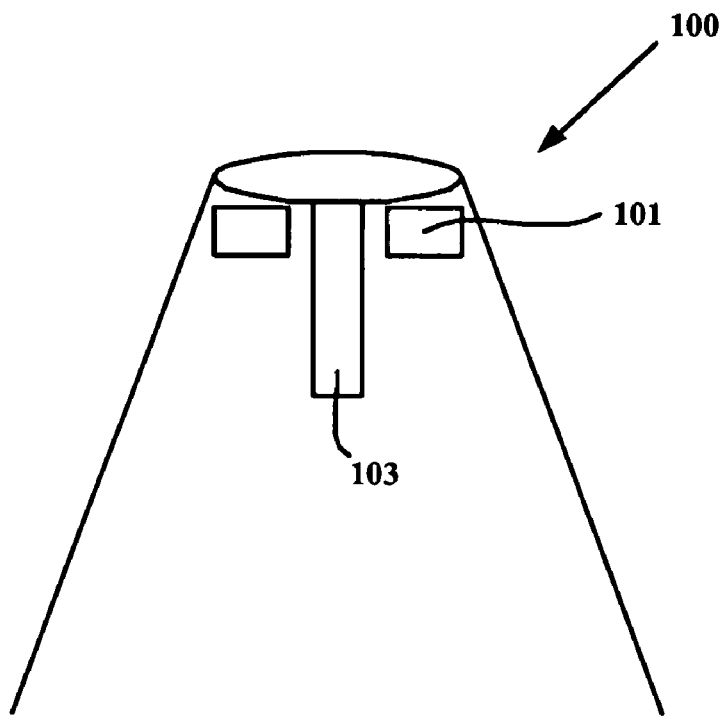

In one aspect of the invention, the source and detector can be configured close to the sample when it is part of the XRF device. Such a configuration is illustrated in FIG. 12. FIG. 12 depicts the "nose" or tip of the XRF device 100 where the detector 103 has been moved to the center of the nose. The source (or sources) 101 are then disposed proximate the detector near the tip of the XRF device. With closer geometries between the source and detector, better control of the data can be obtained, and a more efficient use of the EMRXG source is realized.

Configuring the device as illustrated in FIG. 12 also allows the device to be located closer to the sample during operation. The distance between the source of the XRF device and the sample in the invention can range, in one embodiment, from about 0.05 cm to about 1.0 cm, in another embodiment from about 0.05 cm to about 0.2 cm, and in another embodiment is about 0.1 cm. This closer proximity is possible because at these distances, the sample can still be excited by the desired number of EMRXG emitted from the source. In this closer arrangement, the operation of the XRF device becomes a near field application rather than a far field application. Thus, the path lengths of the x-rays are measured as a few millimeters instead of tens of millimeters. Thus, the exitation and collection efficiency increases by an order of magnitude of about 2 to about 3.

In another aspect of the invention, the source and detector can be configured close to the sample by being an attachment (or part of an attachment) for the XRF device. For example, the source and detector can be part of a washer that is used at the tip of the XRF device near the sample. In another example, the source and detector can be part of a vacuum attachment that is used at the tip of the XRF device in a vacuum XRF method. See, for example, the disclosure of U.S. patent application Ser. No. 10/307,191, the disclosure of which is incorporated herein by reference.

The shape and size of the source, as well as the detector, can be varied for the desired EMRXG impingement on the sample and the detector. There are numerous sizes and shapes that can be used depending on the size and shape of the sample and detector. Examples of the sizes and shapes that can be used are illustrated in FIGS. 8-11 where the source is proximate the detector, spaced about the detector, or surrounding the detector.

Figure 10:
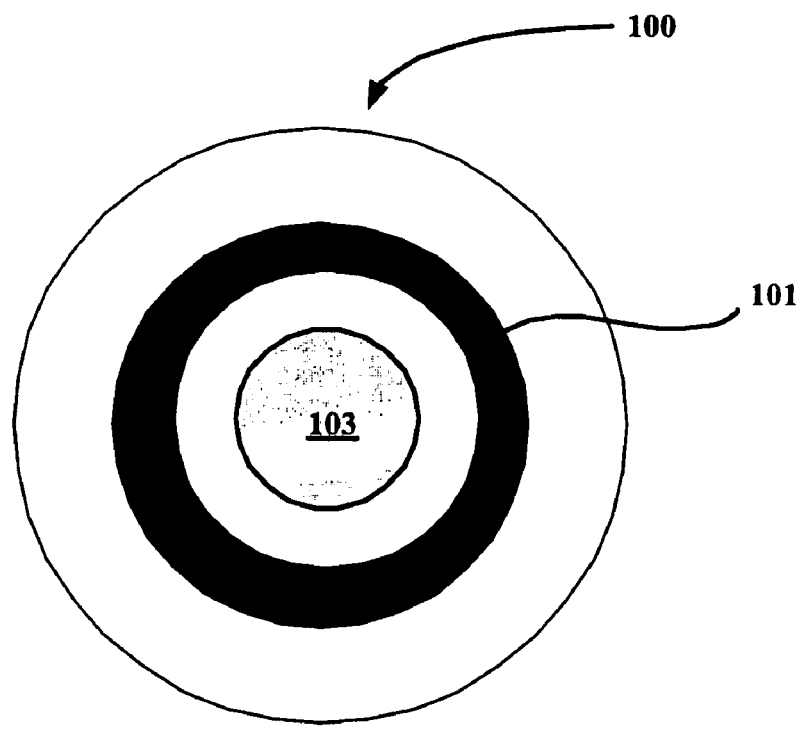
Figure 11:
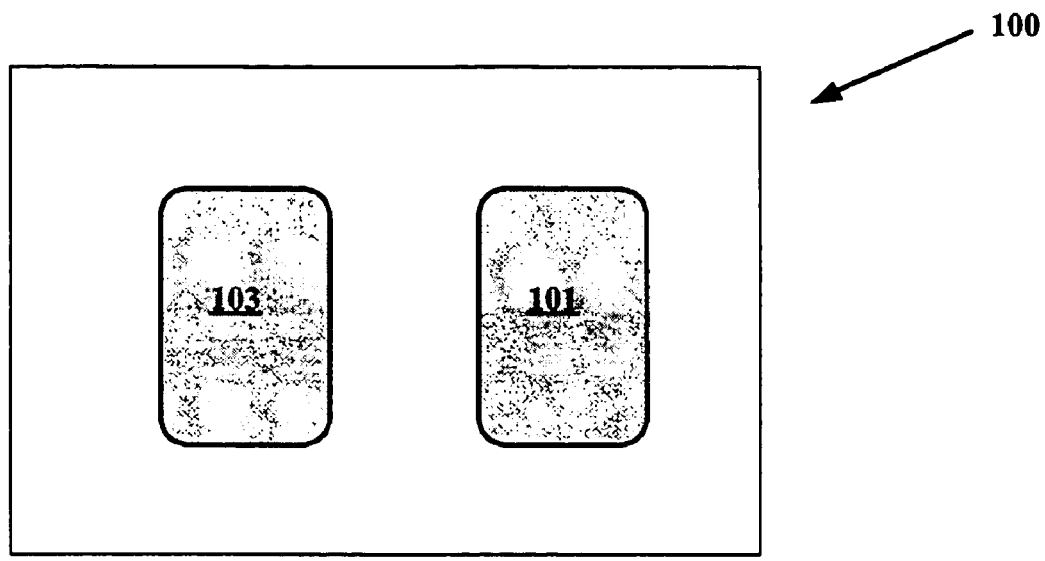

In one aspect of the invention, the source 101 and detector 103 are configured as illustrated in FIG. 10 in the shape of a ring surrounding the detector. In this configuration, the efficiency of the EMRXG striking the sample and the detector are optimized. This ring configuration is able to provide an optimum efficiency.

With the invention, the types (and amounts) of materials that can be used as the EMRXG source increase when compared with those previously used. The types (and amounts) of materials that can be used in prior devices were limited by the large amounts of EMRXG that had to be produced. With the invention, the amounts of EMRXG that need to be produced for fluorescence analysis are diminished. Thus, any material that produces lower number of EMRXG can be used in the invention. As well, since the source need produce less EMRXG, lower amounts of conventional radioactive materials can be used in the invention.

Some non-limiting examples of radiation materials that can be used include, $Co^{57}$, $Am^{241}$, $Cd^{109}$, and $Fe^{55}$. In one embodiment, the amount of $Co^{57}$ is about 1 µCi to about 100 µCi, and in another embodiment from about 1 µCi to about 50 µCi. In one embodiment, the amount of $Am^{241}$ is about 1 µCi to about 50 µCi., and the amount of $Cd^{109}$ is about 1 µCi to about 50 µCi. In one embodiment, the amount of $Fe^{55}$ is about 1 µCi to about 100 µCi, and in another embodiment, about 1 µCi to about 50 µCi. In alternate embodiments, $Gd^{53}$, $Ni^{63}$, $Eu^{155}$, and $Cm^{244}$ can be used in amounts ranging from about 1 µCi to about 100 µCi.

In known XRF devices the amount of $Co^{57}$ used is about 25 mCi, the amount of Am 241 used is about 100 mCi, the amount of $Cd^{109}$ is about 30 mCi, and the amount of $Fe^{55}$ is about 30 mCi. As can be seen, the amount of radioactive material used in XRF device 100 (shown in FIG. 12) is significantly less than known XRF devices. The quantity of radioactive material considered exempt by the Nuclear Regulatory Commission (NRC) is 100 µCi or less, for $Co^{57}$, 1 µCi to 50 µCi for $Am^{241}$, 10 µCi or less for $Cd^{109}$, and 100 µCi for $Fe^{55}$.

Using the invention provides several advantages. First, the XRF device is much less expensive to make and maintain. Without a source block, and with the increased options of different source materials and smaller amounts, the manufacturing cost is decreased drastically. The XRF devices are also less expensive to maintain because of the elimination of the government licensing requirements.

A second advantage is a decreased size (and weight). By eliminating the source block and moving the source nearer the detector (and the accompanying reconfiguration of the remainder of the components), the size of the device can be decreased by about 50%. Indeed, with a smaller size, the shape can be modified for any desired shape, e.g., similar to a handheld television remote control or a pen with an umbilical connection to a box the size of a computer mouse. The weight of the XRF device can be decreased substantially, for example., in one embodiment, by about 60% to about 80% from about 5 pounds to less than about 2 pounds, and in another embodiment to about 1 pound. With a decreased size and weight, the XRF device of the invention can be used in smaller or tighter areas that larger XRF devices can access.

Another advantage of the invention is better resolution of the data. The tight configuration between the source, detector, and sample (and the smaller distances between them) aids the capability of aperturing between them. With this capability comes a very large transmission of the photons to a smaller area on the detector that results in better resolution of the photon signals. As well, the noise floor can be improved because photons are not impinging on non-active areas of the detector.

The device described above is a small handheld instrument that is extremely portable, yet very powerful, for XRF analysis. The device of the invention is not limited to any specific XRF analysis. Any type of XRF, such as total reflection x-ray fluorescence (TXRF) or energy-dispersive x-ray fluorescence (EDXRF), can be employed in the invention.

Having described the preferred aspects of the invention, it is understood that the invention defined by the appended claims is not to be limited by particular details set forth in the above description, as many apparent variations thereof are possible without departing from the spirit or scope thereof.

What is claimed is:

1. An XRF device comprising:
   an internal housing containing a detector for high energy radiation; and
   a high energy radiation source contained within said same internal housing, said high energy radiation source and said detector proximate each other near a sensing end of said device, wherein an emitting end surface of said high energy radiation source defines a plane extending from and parallel to said emitting end surface, and a receiving end surface of said detector is parallel to said plane and is substantially positioned in said plane, and wherein said XRF device does not include a separate shield between said detector and said high energy radiation source.

2. A device in accordance with claim 1 wherein said high energy radiation source comprises a EMRXG source.

3. A device in accordance with claim 2 wherein said EMRXG source comprises an exempt amount of a radioactive material.

4. A device in accordance with claim 2 wherein said EMRXG source comprises $Gd^{53}$, $Ni^{63}$, $Eu^{155}$, or $Cm^{244}$.

5. A device in accordance with claim 1 wherein said radioactive material comprises $Co^{57}$, $Am^{241}$, $Cd^{109}$, or $Fe^{55}$.

6. A device in accordance with claim 5 wherein said radioactive material comprises an amount ranging from about 1 µCi to about 100 µCi.

7. A device in accordance with claim 5 wherein said radioactive material comprises an amount ranging from about 1 µCi to about 50 µCi.

8. A device in accordance with claim 1 wherein said high energy radiation source is spaced about said detector.

9. A device in accordance with claim 1 wherein said high energy radiation source surrounds said detector.

10. A portable XRF device comprising:
    an internal housing containing a detector for high energy radiation; and
    a high energy radiation source contained within said same internal housing, said high energy radiation source comprising from about 1 µCi to about 100 µCi. of a radioactive material;
    said source and said detector are proximate each other near a sensing end of the device, wherein an emitting end surface of said high energy radiation source defines a plane extending from and parallel to said emitting end surface, and a receiving end surface of said detector is parallel to said plane and is substantially positioned in said plane, and wherein said XRF device does not include a separate shield between said detector and said high energy radiation source.

11. The device of claim 10, wherein the source is spaced about the detector.

12. A device in accordance with claim 11 wherein said source surrounds said detector.

13. A device in accordance with claim 10 wherein said radioactive material of said source comprises $Co^{57}$, $Am^{241}$, $Cd^{109}$, or $Fe^{55}$.

14. A device in accordance with claim 10 wherein said radioactive material of said source comprises $Gd^{53}$, $Ni^{63}$, $Eu^{155}$, or $Cm^{244}$.

15. A method for analyzing a sample, said method comprising:
    providing a sample;
    providing an XRF device comprising a internal housing containing both a high energy radiation source and a high energy radiation detector, the high energy radiation source comprising a radioactive material, the high energy radiation source and the detector proximate each other near a sensing end of the device, wherein an emitting end surface of the high energy radiation source defines a plane extending from and parallel to the emitting end surface, and a receiving end surface of the detector is parallel to the plane and is substantially positioned in the plane, and wherein the XRF device does not include a separate shield between the detector and the high energy radiation source; and
    analyzing the sample using the XRF device.

16. A method in accordance with claim 15 wherein the XRF device both impinge the sample with an EMRXG and detects an x-ray fluoresced by the sample.

17. A method in accordance with claim 15 wherein the sample contains a taggant and the XRF device both impinges the taggant with EMRXG and detects an x-ray fluoresced by the taggant.

18. A method in accordance with claim 15 wherein the high energy radiation source comprises an exempt quantity of the radioactive material.

19. A method in accordance with claim 15 wherein the high energy radiation source is spaced about the detector.

20. A method in accordance with claim 19 wherein the high energy radiation source surrounds the detector.

21. A method in accordance with claim 15 wherein the radioactive material of the source comprises $Co^{57}$, $Am^{241}$, $Cd^{109}$, or $Fe^{55}$.

22. A method in accordance with claim 15 wherein the radioactive material comprises an amount ranging from about 1 µCi to about 100 µCi.

23. A method in accordance with claim 15 wherein the radioactive material of the source comprises $Gd^{53}$, $Ni^{63}$, $Eu^{155}$, or $Cm^{244}$.

24. A method for analyzing a sample, said method comprising:
    providing a sample;
    providing an XRF device comprising an internal housing containing both an EMRXG source and an x-ray detector, the EMRXG source comprising a radioactive material; an emitting end of the source and a receiving end of the detector proximate each other near a sensing end of the XRF device with the EMRXG source surrounding the detector, wherein an emitting end surface of the high source defines a plane extending from and parallel to the emitting end surface, and a receiving end surface of the detector is parallel to the plane and is substantially positioned in the plane, wherein the XRF device does not include a separate shield between the detector and the EMRXG source; and
    analyzing the sample using the XRF device, wherein the XRF device both irradiates the sample with EMRXG from the source and detects x-rays fluoresced by the sample.

25. A method in accordance with claim 24 wherein the sample contains a taggant and the XRF device both impinges the taggant with EMRXG from the source and detects x-rays fluoresced by the taggant.

* * * * *